United States Patent

Miller

[11] 3,980,082
[45] Sept. 14, 1976

[54] VENOUS PRESSURE INDICATOR
[76] Inventor: William Miller, 25 Manitou Road, Westport, Conn. 06880
[22] Filed: Mar. 14, 1975
[21] Appl. No.: 558,357

[52] U.S. Cl. .................... 128/214 R; 128/2.05 D; 73/409
[51] Int. Cl.² .................... A61M 5/14; A61B 5/02
[58] Field of Search .................... 128/2.05 D, 214 R; 73/409

[56] References Cited
UNITED STATES PATENTS

| | | | |
|---|---|---|---|
| 2,625,153 | 1/1953 | Baum | 128/2.05 D |
| 3,584,770 | 6/1971 | Taylor | 128/214 R X |
| 3,610,230 | 10/1971 | Andersen | 128/2.05 D |
| 3,690,318 | 9/1972 | Gorsuch | 128/214 E |
| 3,890,962 | 6/1975 | Ramsey | 128/2.05 D |
| 3,895,533 | 7/1975 | Steier | 73/409 |

Primary Examiner—Dalton L. Truluck

[57] ABSTRACT

An intravenous infusion system combined with a venous pressure measuring instrument whereby the system is selectively capable of supplying fluid into the vein of a patient or of measuring his venous pressure without, however, exposing fluid in the system to the atmosphere and possible contamination. The instrument includes a transparent chamber interposed between an upstream line extending to the infusion fluid supply and a downstream line leading to the patient. A collapsible bulb disposed within the chamber is vented to the atmosphere, the bulb collapsing only when its internal pressure is less than external fluid pressure. In the infusion mode, supply fluid passing through the chamber is fed to the patient, the resultant fluid pressure in the chamber causing the normally-erect bulb to collapse. In the venous pressure mode, the upstream line is clampd to interrupt flow, the fluid pressure then exerted on the bulb being a function both of venous pressure and the height of the chamber relative to the heart, the higher the chamber the lower the pressure. By elevating or lowering the chamber to a point at which fluid pressure therein is equal to atmospheric pressure, a balance or reference pressure level is established, this level being indicated by the sudden erection or collapse of the bulb, depending on whether the bulb is moving upward or downward. Venous pressure is then determined by measuring the height of the chamber at this level along a scale formed on the downstream line.

9 Claims, 5 Drawing Figures

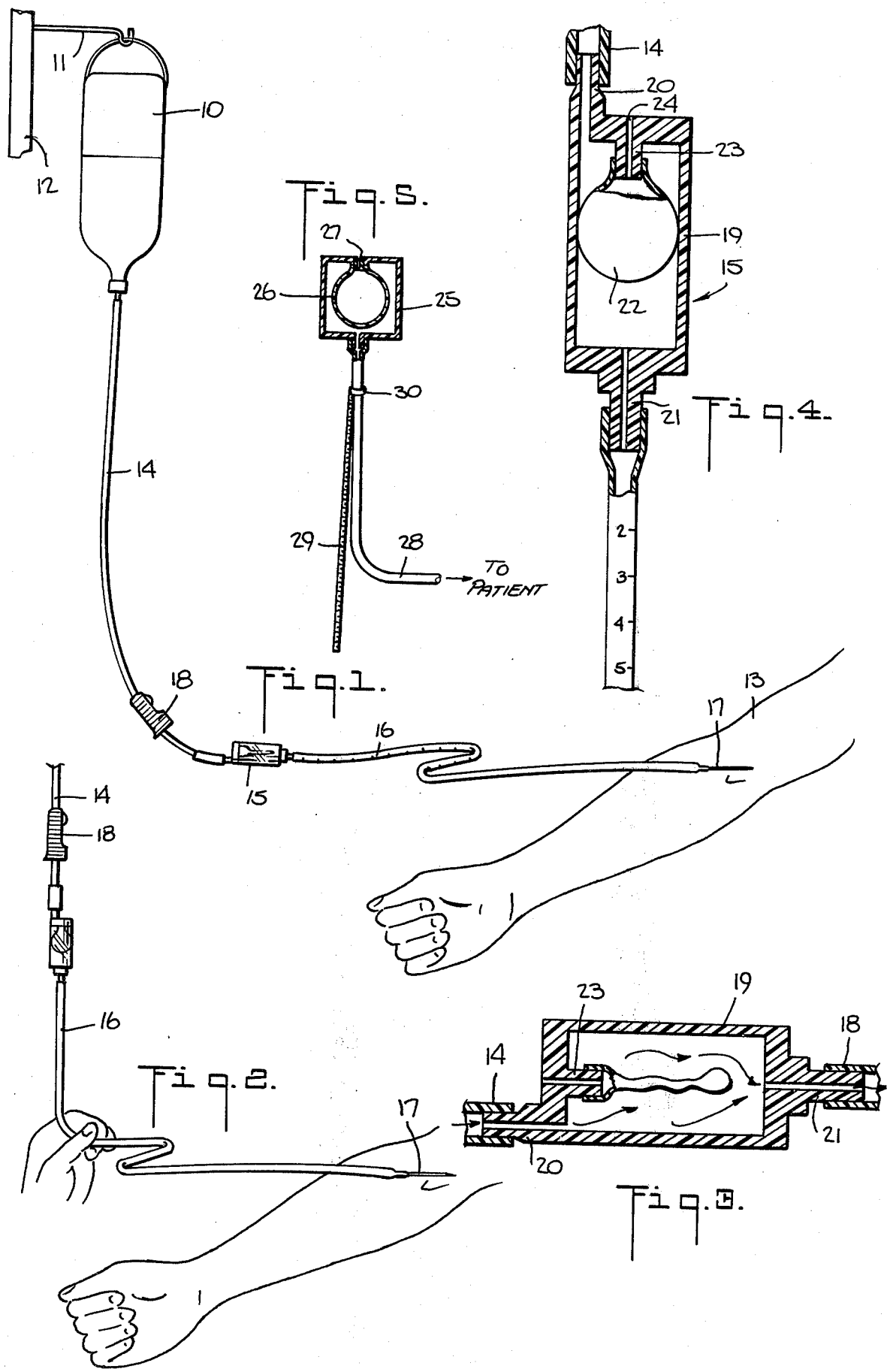

VENOUS PRESSURE INDICATOR

BACKGROUND OF INVENTION

This invention relates generally to venous pressure measuring instruments, and more particularly to a simple, easily-operated device adapted to measure venous pressure in a flow system which is sealed from the atmosphere.

During many surgical procedures as well as in post-operative stages, it is now the usual practice to measure and record venous pressure. Venous pressure trends are a significant consideration in both diagnosis and prognosis. Moreover, such measurement is also important with respect to cardiovascular diseases, for an upward trend is one of the first signs of congestive heart failure.

The most commonly-used venous pressure measuring instrument is of the manometer type and includes a three-way stopcock and an intravenous needle to provide an arm puncture. The longitudinal passage in the stopcock connects the needle to a syringe, while its vertical outlet is coupled to the graduated manometer tube. In operation, blood is first drawn into the syringe which contains a sterile saline solution. After manipulation of the stopcock valve, the manometer tube is filled by expressing the mixture from the syringe. Thereafter, communication is restored between the manometer tube and the vein. This manometer, stop-cock combination may be used as part of an intravenous infusion apparatus, in which case the longitudinal passage in the stopcock connects the needle to the fluid supply, and the vertical outlet is coupled to the graduated manometer tube. During normal feeding, the fluid supply is connected to the needle, and the manometer tube is isolated. To read the pressure, the stopcock is first turned until the fluid supply is connected to the manometer (to flush the manometer), after which the stopcock is turned to connect the manometer to the needle. After the pressure is read, the needle is re-connected to the fluid supply.

The level to which liquid in the manometer falls upon reaching equilibrium is read directly from the tube scale, thereby providing a venous pressure reading. It will be recognized that the operating procedure for the manometer is somewhat complicated. Also, to obtain a correct reading, care must be exercised, and for this purpose the base of the manometer must be properly aligned with an appropriate point on the patient's body.

Venous pressure can vary through a relatively wide range, from a low of zero (or even negative values) relative to atmospheric pressure to a high of 25 or 30 cm of water above atmospheric pressure. As a consequence, the conventional venous pressure instrument requires a fairly long manometer tube as well as associated apparatus that must be carefully assembled and properly supported. Because the upper end of the manometer tube is open to the atmosphere, the fluid is exposed and may be subject to bacterial contamination that is transmittable to the patient.

The intravenous (IV) infusion of various types of fluids to patients is a routine hospital procedure. In a standard IV system, a plastic bottle filled with a fluid such as glucose, serum or plasma, is supported at an elevated position to provide gravity flow through a flexible line whose end is coupled to a needle injected into a vein of the patient. In practice, there are many situations in which it is desirable to be able to infuse fluid into a patient or to take a venous pressure reading, using the same line for this purpose.

This requirement is met in the Anderson U.S. Pat. No. 3,610,230, wherein a manometer is used to indicate vein pressure by observation of a column of liquid in continuous communication with the vein, combined with means for infusing fluid therein. But since this combination entails a supported manometer tube, it exhibits the disadvantages characteristic of such arrangements.

The Miller et al. U.S. Pat. No. 3,807,389 discloses a venous pressure instrument that is interposable in an IV system, the instrument including a valve chamber vented to the atmosphere. In one position of the valve, normal infusion into the patient is permitted, while in another valve position infusion is interrupted to admit a return flow of pressurized fluid from the patient, in a manner causing pressurized fluid to flow into a graduated capillary tube to afford a venous pressure reading.

The Miller et al. instrument is therefore adapted selectively to effect normal intravascular infusion or to measure venous pressure. This instrument has the advantage of requiring no stand or other support, but it does entail a valve, and because of its air vent it is subject to possible bacterial contamination.

SUMMARY OF INVENTION

In view of the foregoing, it is the main object of this invention to provide a venous pressure measuring instrument which is interposable in an intravenous infusion line or is usable separately therefrom to effect venous pressure measurement without exposing any of the fluid to the atmosphere, thereby avoiding the possibility of contamination.

More particularly, it is an object of the invention to provide a venous pressure measuring instrument which is interposed in a flexible infusion line leading to a patient, the downstream portion of the line functioning effectively as a manometer column, thereby dispensing with a supported manometer tube and the need to align the base of a remote manometer tube with a point on the patient's body.

Also an object of the invention is to provide a venous pressure measuring instrument which is of exceptionally simple construction, which is relatively inexpensive to manufacture and which may be operated and read without difficulty.

Briefly stated, these objects are attained in an intravenous system including a venous pressure measuring instrument, whereby the system is selectively capable of feeding a therapeutically-useful fluid into the vein of a patient or of measuring his venous pressure. The instrument is constituted by a transparent chamber interposed between an upstream line extending to the bottle containing the infusion fluid and a downstream line leading to a cannula.

Visibly disposed within the chamber is a collapsible bulb that is vented to the atmosphere, the bulb being erected when the fluid pressure exerted on its exterior is not greater than atmospheric, the bulb collapsing when fluid pressure is greater than atmospheric. Because the vent communicates only with the interior of the bulb, the fluid in the system is sealed from the atmospheric and contamination thereof is avoided.

In the infusion mode, fluid derived from the bottle and going to the patient passes through the chamber, and the resultant fluid pressure exerted in the bulb causes it to collapse. In the venous pressure mode, the upstream line is clamped to block flow from the bottle, as a result of which the fluid pressure then exerted on the bulb is a function both of venous pressure and the height of the chamber relative to the heart, the higher the chamber the lower the fluid pressure.

By elevating the chamber to a point at which the fluid pressure exerted on the bulb is equal to atmospheric pressure, a balance or reference level is established, this balance level being indicated by the sudden erection of the bulb. Venous pressure is then determined by measuring the height of the chamber at the balance level relative to the heart, this measurement being made on a scale formed on the downstream line.

In another embodiment of the invention, the instrument is independent of an IV system, in which instance the chamber has no inlet but only a flexible line connection to the patient. The balance level is attained when the elevation of the chamber is such that at the interface of the air compressed in said line and the fluid derived from a body cavity, the pressures are equal, the body pressure being determined by measuring the height between the interface at the balance level and the body point.

OUTLINE OF DRAWING

For a better understanding of the invention as well as other objects and further features thereof, reference is made to the following detailed description to be read in conjunction with the accompanying drawing, wherein:

FIG. 1 illustrates, in perspective, an intravenous infusion system incorporating a venous pressure measuring instrument in accordance with one preferred embodiment of the invention;

FIG. 2 illustrates the manner in which a venous pressure measurement is taken;

FIG. 3 is a sectional view of the instrument, with its bulb in the collapsed state.

FIG. 4 is a sectional view of the instrument but with the bulb in its erect state; and FIG. 5 shows an embodiment of the venous pressure measuring instrument which is independent of an intravenous infusion system.

DESCRIPTION OF INVENTION

Structure of First Embodiment

Referring now to FIGS. 1 to 4, there is shown an intravenous infusion system including an inverted bottle 10 containing a solution such as glucose. The bottle is suspended by means of a hook 11 extending from a stand 12. The IV system is conventional and may include a drop chamber and other elements not shown.

Because of gravity flow, the fluid in the bottle, which is elevated above a patient whose arm 13 is shown, passes down through a line 14 that is coupled to the inlet of a venous pressure measuring device, generally designated by numeral 15. The instrument includes a line 16 connected to the outlet of the device and coupled to a needle or cannula 17 which is injected in the vein of the patient.

Lines 14 and 16 are formed by flexible plastic tubing of the type used in standard IV sets. Since line 14 is on the upstream side of venous pressure device 15, it will hereafter be referred to as the upstream line, and since line 16 is on the downstream side, it will hereinafter be referred to as the downstream line. Installed on upstream line 14 is an on-off clamp 18 which, when closed, blocks flow from the bottle into venous pressure measuring device 15. In practice one may dispense with the clamp and, when necessary, simply pinch the line with the fingers to interrupt flow.

As best seen in FIGS. 3 and 4, venous pressure measuring device 15 is constituted by a generally cylindrical chamber 19 formed of rigid, transparent plastic material. The upper end of chamber 19 is provided with an inlet fixture 20 to which upstream line 14 is connected, this fixture being adjacent the periphery of the chamber. Projecting from the center of the lower end of chamber 19 is an outlet fixture 21 to which downstream line 16 is connected. For reasons which will be later explained, line 16 is provided with indicia along its length so that it can also function as a measuring scale.

Visibly disposed within chamber 19 is a generally spherical bulb 22 formed of a thin, flexible membrane. Such membranes are frequently mass-produced by latex-dipping processes. It will be appreciated that all elements of the system, including lines 14 and 16, chamber 19 and bulb 22, must be fabricated of sterile material which is non-reactive with the fluids passing therethrough.

Bulb 22 is suspended within chamber 19 by bonding its mouth to the outer surface of an internal fixture 23 having a longitudinal bore which communicates with the atmosphere. Thus the interior of bulb 22 is at atmospheric pressure, whereas the exterior thereof is subjected to the existing fluid pressure within chamber 19. The chamber itself is not vented.

The physical characteristics of the bulb are such that when the internal pressure, which is atmospheric, is equal to or greater than external fluid pressure, the bulb assumes its erect or normal configuration, but when the external pressure exceeds internal pressure, then the bulb will flatten out or collapse. Thus FIG. 3 shows the bulb in its collapsed state, while in FIG. 4 the bulb is shown in its erect state. The transition from the collapsed state to the erect state is abrupt and dramatic, for the moment the internal and external pressures become equal, the bulb pops out. The bulb is preferably formed of opaque and distinctly colored material so that its state may readily be observed through the wall of the chamber.

Operation of Device

In the intravenous infusion mode, clamp 18 on upstream line 14 is open, thereby permitting flow of infusion fluid from bottle 10 and through line 14, chamber 19 and line 16 into the vein of the patient.

Because of the column of fluid in the upstream line 14, the resultant fluid pressure within chamber 19 which is exerted on the exterior of bulb 22 is greater than the atmospheric pressure within the bulb. As a result, in the infusion mode, the bulb is flattened or collapsed and the passage through chamber 19 is unobstructed so that feeding of the fluid takes place in the same manner as would occur in the absence of the venous pressure measuring device.

If now one wishes to take a venous pressure reading, clamp 18 is closed to interrupt the supply of fluid to the patient. In the venous pressure mode, fluid pressure within chamber 19 is independent of the fluid column in upstream line 14. The pressure which now exists at all points in the system extending between the clamp position and the patient and including chamber 19 is a function both of the intravascular fluid pressure in the patient and the height of the point in question relative to the patient's heart.

Let us by way of example consider a particular point in the system when operating in the venous pressure mode that is 6 cm above the heart of the patient. Let us further assume that the patient's heart is at 13 cm $H_2O$. Hence the pressure at the particular point is 7 cm $H_2O$, the difference between 13 cm and 6 cm.

If, therefore, bulb 22 is positioned at this particular point, it will be subjected to an external pressure of 7 cm $H_2O$. And if bulb 22 is now lowered so that it is disposed 3 cm below the level of the heart, then fluid pressure exerted thereon will be 16 cm $H_2O$, the sum of the heart pressure, 13 cm $H_2O$, and 3 cm. On the other hand, if the bulb 22 is positioned at a point 17 cm above the patient's heart, the pressure exerted on the bulb by the fluid will be 4 cm $H_2O$ less than atmospheric pressure.

It is clear then, that for a given venous pressure, the bulb will be in an erect state when it is above a certain level, and in a collapsed state when below this level, and the level at which the transition takes place is the level at which the fluid pressure on the bulb is equal to atmospheric pressure.

For determining venous pressure, chamber 19, which is held in the hand of the operator, is slowly moved vertically above or below the heart of the patient until a point is reached at which the fluid pressure exerted on bulb 22 is in balance with the atmospheric pressure within the bulb.

Before this balance point is reached, the fluid pressure, which depends on venous pressure, is greater or less than atmospheric, hence the bulb is correspondingly in a collapsed or erect state. But the moment the point is passed at which internal and external pressures are equal, the bulb suddenly changes state. Since bulb 22 is visible through the wall of chamber 19, the sudden transition of state provides a striking indication of the reference point. Having established this reference point, one can now determine the pressure at any other point along the downstream line 16 by measurement of the height difference.

This is done by means of the graduated scale formed along downstream line 16, whose markings are in terms of cm. All that need be done while holding chamber 19 at the reference level with one hand is to grasp downstream line 16 between the thumb and forefinger of the other hand and to slide these fingers along this line until a measuring point on the line is reached which corresponds to the level of the heart, as illustrated in FIG. 2. By reading the scale at this measuring point, one obtains a reading of venous pressure.

The flexible downstream line, therefore, effectively behaves in the venous pressure mode as a manometer tube. The centimeter scale of this line has its low end at the point of connection to chamber 19, for the greater the vertical distance that the chamber is above the measuring point, the larger the value of venous pressure. Thus the readings increase as the measuring point advances along the downstream line toward the patient. After the venous pressure reading is taken, one simply re-opens the clamp 18 to resume intravenous feeding. Should venous pressure be below atmospheric pressure, the chamber will be below the heart level at balances, and reading will be taken upward along the downstream line.

It is important to note that while the downstream line functions effectively as a manometer tube, its upper end is not exposed to the atmosphere, as in a conventional tube, for this end communicates with chamber 19 which is sealed from the atmosphere. Hence the possibility of bacterial contamination is avoided.

It is necessary that no air bubbles be trapped in the upstream line 14. This can be avoided if during the initial filling of line 14 with the infusion fluid, the line is bent into a U-formation so that fluid entering chamber 19 is forced to flow upwardly into this chamber, thereby expelling all air from the line.

Second Embodiment

In some instances, there is no need to combine a pressure indicator with an IV set, for all that is called for is a pressure measurement. The embodiment disclosed in FIG. 5 serves this purpose, the measuring device in this instance including a transparent chamber 25 having a collapsible bulb 26 therein which is vented to the atmosphere through an opening in the internal fixture 27 from which the bulb is suspended. The chamber is coupled to the patient through a transparent flexible line 28 whose other end is attached to a suitable needle or to whatever other expedient is used to effect coupling to that region or cavity of the body whose pressure is to be measured.

A centimeter scale is printed on a flexible tape 29 whose "zero" end is attached to a ring 30. Ring 30 frictionally engages line 28 so that the ring, though slidable along the line, will remain at any set position thereon.

When the air-filled line 28 is coupled to the patient, fluid will be forced therein. The fluid flows into the line until the air trapped therein is compressed to a degree where the resultant air pressure in the line at the interface between air and fluid matches fluid pressure. As one raises chamber 25, the fluid column in the line extending between the air-fluid interface and the patient will decrease. Thus the higher the level to which the chamber is raised, the lower is the fluid pressure at the interface, thereby reducing air compression in the line.

In operation, as one slowly raises the chamber above the level of the patient, a point is reached at which the compressed air pressure at the air-fluid interface reaches atmospheric. At this point, bulb 26, which up to this point has been in its collapsed state because the air pressure applied externally thereto in chamber 25 exceeded its internal atmospheric pressure, suddenly pops out, indicating that the internal and external bulb pressures in the chamber are in balance.

At this elevation of the chamber, the interface point in the line is at atmospheric pressure. With this as a reference, one can by means of tape 29, whose ring is then set to be coincident with the reference point, read the distance between the reference point and the patient level.

As an alternative, one can graduate line 28 and thereby dispense with the measuring tape 29. But then one would have to deduct from the scale reading which gives the height of the chamber above the pressure point on the patient, the distance between zero on the scale and the level of the air-fluid interface on the line.

While there have been shown and described preferred embodiments of a venous pressure measuring instrument in accordance with the invention, it will be appreciated that many changes and modifications may be made therein without, however, departing from the essential spirit thereof. The term "venous pressure," as used herein, normally refers to central venous pressure but can also mean peripheral venous pressure.

I claim:

1. A medical instrument usable in conjunction with an intravascular infusion system having a fluid source and selectively adapted to effect normal intravascular infusion or to measure intravascular fluid pressure, said instrument comprising:
   A. a transparent chamber having an inlet and an outlet and having a collapsible bulb mounted therein, the interior of the bulb being vented to the atmosphere and the exterior thereof being subject to the fluid pressure existing within the chamber, whereby said bulb assumes an erect state when said fluid pressure is no greater than atmospheric and assumes a collapsed state when said fluid pressure is greater than atmospheric;
   B. a flexible upstream line connecting the inlet of said chamber to said fluid source and a flexible downstream line connecting the outlet of said chamber to said patient whereby, in the infusion mode, fluid from said source flows through said upstream line into said chamber and from said chamber through said downstream line into said patient;
   C. means, in the pressure measuring mode, to clamp said upstream line to block flow of infusion fluid, said chamber then being elevated to a balance level above or below said patient at which the fluid pressure in said chamber equals atmospheric pressure, as indicated by the sudden erection or collapse of said bulb; and
   D. means to measure the height of said balance level to determine the intravascular pressure.

2. An instrument as set forth in claim 1, wherein said bulb is mounted within said chamber on an internal fixture having a bore communicating with the atmosphere.

3. An instrument as set forth in claim 1, wherein said clamping of said upstream line is effected by an on-off clamp installed on said line.

4. An instrument as set forth in claim 1, wherein said height measuring means is constituted by a graduated scale formed on said downstream line.

5. An instrument as set forth in claim 1, wherein said source is constituted by an inverted bottle suspended from a stand.

6. An instrument as set forth in claim 1, wherein said bulb is formed by distinctively colored film material.

7. A medical instrument to measure the pressure in a body cavity, said instrument comprising a transparent chamber having a collapsible bulb mounted therein, the interior of the bulb being vented to the atmosphere through an opening in the chamber, whereby the interior of the bulb is at atmospheric pressure and the exterior thereof is subject to the existing fluid pressure within the chamber, a flexible tube for connecting said chamber to said body cavity, and means to determine the height of the fluid level in said tube above the point in the body cavity whose pressure is being measured when the pressure within said bulb is substantially equal to the pressure within said chamber to provide a pressure indication.

8. An instrument as set forth in claim 7, wherein said means to determine the height of the fluid level includes a measuring tape, one end of which is attached to a ring which is frictionally coupled to said tube, whereby the ring may be shifted thereon and set to coincide with the interface between air in said tube and fluid derived from the body cavity.

9. An instrument as set forth in claim 7, wherein said tube has a scale formed thereon to facilitate said determination.

* * * * *